United States Patent
Kohn et al.

(10) Patent No.: US 9,511,147 B2
(45) Date of Patent: Dec. 6, 2016

(54) INTERPOLYMER NETWORK DELIVERY SYSTEM

(75) Inventors: Joachim B. Kohn, Piscataway, NJ (US); Carmine P. Iovine, Bridgewater, NJ (US); Niraj Ramachandran, West Lafayette, IN (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/238,605

(22) PCT Filed: Aug. 12, 2012

(86) PCT No.: PCT/US2012/050493
§ 371 (c)(1),
(2), (4) Date: Jun. 2, 2014

(87) PCT Pub. No.: WO2013/025572
PCT Pub. Date: Feb. 21, 2013

(65) Prior Publication Data
US 2014/0308331 A1    Oct. 16, 2014

Related U.S. Application Data

(60) Provisional application No. 61/522,880, filed on Aug. 12, 2011.

(51) Int. Cl.
| | | |
|---|---|---|
| *A61K 9/70* | (2006.01) | |
| *A61L 31/16* | (2006.01) | |
| *A61K 33/18* | (2006.01) | |
| *A61K 47/36* | (2006.01) | |
| *A61K 45/06* | (2006.01) | |
| *A61K 47/32* | (2006.01) | |
| *A61L 31/04* | (2006.01) | |
| *C08G 18/83* | (2006.01) | |

(52) U.S. Cl.
CPC ............. *A61K 47/36* (2013.01); *A61K 9/7023* (2013.01); *A61K 33/18* (2013.01); *A61K 45/06* (2013.01); *A61K 47/32* (2013.01); *A61L 31/042* (2013.01); *A61L 31/048* (2013.01); *A61L 31/16* (2013.01); *C08G 18/831* (2013.01)

(58) Field of Classification Search
None
See application file for complete search history.

(56) References Cited

U.S. PATENT DOCUMENTS

| | | | |
|---|---|---|---|
| 3,235,446 | A | 2/1966 | Shelanski et al. |
| 4,381,380 | A | 4/1983 | LeVeen et al. |
| 4,769,013 | A | 9/1988 | Lorenz et al. |
| 4,931,282 | A | 6/1990 | Asmus et al. |
| 5,302,392 | A | 4/1994 | Karakelle et al. |
| 6,416,740 | B1 | 7/2002 | Unger |
| 6,607,748 | B1 * | 8/2003 | Lenaerts ............ A61K 9/2059 424/464 |
| 2005/0238686 | A1 | 10/2005 | Hossainy et al. |
| 2007/0166344 | A1 | 7/2007 | Qu et al. |
| 2007/0197957 | A1 | 8/2007 | Hunter et al. |
| 2007/0275258 | A1 * | 11/2007 | Ohnishi et al. ............... 428/532 |
| 2010/0113619 | A1 * | 5/2010 | Brouillet et al. ............. 514/778 |
| 2010/0150989 | A1 * | 6/2010 | Hoffman et al. ............. 424/445 |
| 2010/0178358 | A1 * | 7/2010 | Gastonguay et al. ........ 424/622 |

OTHER PUBLICATIONS

Balmayor et al., "Preparation and characterization of starch-poly-e-caprolactone microparticles incorporating bioactive agents for drug delivery and tissue engineering applications," Acta Biomaterialia 5, 1035-1045 (2009).

* cited by examiner

*Primary Examiner* — H. Sarah Park
(74) *Attorney, Agent, or Firm* — Fox Rothschild LLP

(57) ABSTRACT

This invention relates to compositions and applications for an mterpolymer network delivery system containing iodine.

27 Claims, 10 Drawing Sheets

INTERPOLYMER NETWORK DELIVERY SYSTEM

CROSS-REFERENCE TO RELATED APPLICATIONS

The present application claims the benefit of priority under 35 U.S.C. §119(e) of U.S. Provisional Application Ser. No. 61/522,880, filed on Aug. 12, 2011, the entire disclosure of which is incorporated herein by reference.

STATEMENT REGARDING FEDERALLY SPONSORED RESEARCH OR DEVELOPMENT

The invention described herein was supported in whole or in part by grants from the Armed Forces Institute of Regenerative Medicine (Grant No. W81IXWH-0802-0034) and the National Science Foundation Partnership for Innovation (Award No. 0650199). The U.S. Government has certain rights in this invention.

BACKGROUND OF THE INVENTION

Unlike most injuries encountered in hospitals, battlefield wounds are polytraumatic in nature involving multiple mechanisms of injury to multiple anatomical sites. In most of these injuries, contamination is an expected risk and prevention of infection and sepsis is important (Kauvar, D. D. et. al. *J. Burn Care Rehab.,* 26 (2005), 357-61). In the case of burn related injuries, of those with greater than 40% of total body surface area burned, 75% of deaths are related to infectious complications. Furthermore, drug resistant bacteria and fungi are responsible for an increasing number of burn infections (Gamelli, R. L., 13th Annual San Antinio Trauma Symposium, 2007; Schofield, C. M., et. Al., Burns, 33 (2007), 341-346). Many antibiotic drugs and other antimicrobial agents (e.g. silver based compounds, sodium hypochlorite) are currently used in a variety of anti-microbial preparations. However, the use of these compounds has been associated with microbial resistance, allergic potential, tissue toxicity and lack of effectiveness. By preventing or reducing infection, the overall wound healing response will be optimized thus achieving an efficient and beneficial outcome following acute trauma and thermal injuries experienced by today's war fighter. Serious morbidity and mortality from wound infections are not limited to the battlefield. The development of antibiotic resistant bacterial infections in hospitals is now a major health risk to the general population as well.

The ideal infection prevention product would be one that is effective against a broad spectrum of microbes, is biocompatible, does not produce resistant bacteria and has a low potential for developing sensitivity or allergy. Such an approach would utilize the advantages inherent to iodine including the fact that iodine doesn't generate resistant strains of bacteria (Lanker Klossner, B., et. al., *Dermatology,* 195 (1977), Suppl. 2:10-13; Hoang, et. al, *J. Clin. Pathol.* 29 (1976) 753-55). Iodine has continually proven its antimicrobial effectiveness since its introduction almost two centuries ago. Not only is topical iodine effective against all deleterious microbes, it does not produce resistance in bacteria nor does it produce allergies which makes it ideal for traumatic wounds requiring immediate and effective treatment. Research has shown that molecular iodine is the most effective molecular configuration of iodine (Punyani, S., et. al., *J. Appl. Poly. Science* 103 (2007) 3334-3340).

The most commonly used forms of iodine disinfectant are aqueous alcoholic solutions called "tinctures". These typically contain 2-7% molecular iodine along with potassium/sodium iodide in ethanol water mixture. Iodine in this form has many disadvantages including poor stability, high chemical reactivity, odor and skin discoloration and it often irritates and injures skin and wounds. In order to eliminate the disadvantages of "tinctures" iodine has been complexed with water soluble polymeric carriers such as polyvinylpyrrolidone (PVP) and polyvinylalcohol (PVA). Complexes of this type are called iodophors ("Advances in Polymer Science" Vol 108, 1993, 91-129). An iodophor may be defined as a complex of iodine in ionic or molecular form or both with a carrier that serves to increase the solubility of iodine in water and also provides a reservoir of iodine for a controlled and sustained release over time (U.S. Pat. No. 6,565,866, Gottlund, K. L., May 20, 2003). When a polymer is used as the carrier, these complexes are referred to as polymeric iodophors. With water soluble polymer iodophors, the concentration of free iodine in water is reduced due to the formation of micellar aggregates (U.S. Pat. No. 5,071,648, Rosenblatt, S., Dec. 10, 1991). This effect minimizes some of the disadvantages of free iodine found in "tincture" type of disinfectants i.e. odor, irritation and staining of tissue to a large degree.

Although these water soluble polymeric iodophors have an advantage over "tincture" based iodine, they still release to the wound site too quickly because of their stability. Often times, this quick release characteristic provides a much higher dose of iodine than is required for the intended antimicrobial action and the iodine is used up by side reactions with body fluids thus depleting the reservoir prematurely allowing for re-colonization of the wound site. From a clinical point of view, wound dressings based on water soluble polymeric iodophors can only contain low levels of iodine and the dressings need to be changed very frequently in use.

By utilizing a water insoluble polymeric iodophor as the carrier for iodine, the concentration of free iodine in the solution can be maintained at a low level thus avoiding the issues associated with water soluble iodophors including the premature burst like release of the iodine. Many approaches to insoluble polymer iodophors have been reported. Gottlund (U.S. Pat. No. 6,565,866B2, Gottlund, K. L., May 20, 2003) reports on the effective use of various iodine impregnated nylon fiber structures as wound dressings. These materials are not very adsorbent; they release iodine in minutes; and their iodine loading capacity is low. Rosenblatt (U.S. Pat. No. 5,071,648, Rosenblatt, S., Dec. 10, 1991)) and Cercone (U.S. Pat. No. 5,928,665, Cercone, R. J., Jul. 27, 1999) describe broad spectrum anti-microbial dressing materials based on acetalized polyvinylalcohol where PVA, a known water soluble polymeric iodophor, is made insoluble by reaction with aldehydes at substitution levels approaching thirty mole percent. These materials can typically carry up to 8% iodine by weight and this is released slowly over a period of hours. However, the acetalized PVA is unstable in contact with heavily exuding wounds releasing the acetalizing agent slowly over time thus increasing the water solubility of the iodophor and accelerating the release of iodine. Insoluble polyurethane antimicrobial foams and films have been described by Shelanski (U.S. Pat. No. 3,235,446, Shelanski, M. V., Feb. 15, 1966) and LeVeen (U.S. Pat. No. 4,381,380, LeVeen, H. H., Apr. 26, 1983). These materials are stable but can only release iodine over a period of several hours. The iodine is weakly bound to the polymer carrier as a charge transfer complex (Luo, Jie, et. al.

*Journal of Bioactive and Compatible Polymer*. (2010), 25 (2), 185-206) and this accounts for the relatively short duration release characteristics.

There is a need therefore, for an anti-microbial polymeric iodophor that is stable, highly adsorbent, can be loaded with high levels of strongly bound iodine and can release the iodine in a controlled and sustained manner over a period of several days.

SUMMARY OF THE INVENTION

There is provided in accordance with the present invention an interpolymer network delivery system that includes iodine complexed with starch, wherein the starch is covalently bound to a polyurethane polymer. In one embodiment, iodine is present in an amount from about 1% to about 15% by weight of the system. In another embodiment, the starch is present in an amount from about 5% to about 60% by weight of the system.

In yet another embodiment, the starch is derived from a cereal selected from rice, wheat, and maize. In still another embodiment, the starch is derived from a root crop selected from cassava, potato, sweet potato, and arrowroot. In another embodiment, the starch is derived from a source selected from bananas, barley, sago, sorghum, rye, peas, and mung bean.

In one embodiment, the ratio of amylose to amylopectin in the starch ranges from about 50:50 to about 90:10.

In another embodiment, the polyurethane polymer is derived from a polymeric polyol selected from polyether, polyester, polyethylene, polyethylene glycol, polypropylene glycol, and polybutylene glycol polyols.

Also presented is a method for preparing the interpolymer network delivery system by: (a) preparing a mixture that includes at least one polyol and at least one isocyanate compound, wherein the isocyanate compound includes at least two active isocyanate groups per molecule; (b) heating the mixture of step (a) to form a prepolymer solution; (c) mixing the prepolymer solution of step (b) with a starch composition that includes starch and water, (d) curing the mixture of step (c) to form an interpolymer; and (e) contacting the interpolymer of step (d) with an iodine-containing solution.

In one embodiment, the mixture of step (a) further includes a polyurethane catalyst, a solvent, or both. In another embodiment, the starch composition of step (c) further includes a polyurethane catalyst, a surfactant, or both.

In yet another embodiment, the method further includes washing the cured interpolymer of step (d) prior to contacting the interpolymer with the iodine-containing solution. In one embodiment, the iodine-containing solution is selected from an aqueous $KI_3$ solution, $I_2$ in methanol, and $I_2$ in ethanol.

In still another embodiment, the polyol is a polymeric polyol. In yet another embodiment, the polyol is a non-polymeric polyol.

In another embodiment, the isocyanate compound is selected from 2,4-diisocyanatotoluene; 2,6-diisocyanatotoluene; methylenediphenyl 4,4'-diisocyanate; methylenediphenyl 2,4-diisocyanate; methylenediphenyl 2,2'-diisocyanate; 1,5-naphthalene diisocyanate; 4,4',4"-triisocyanatotriphenylmethane; bis(3,5-diisocyanato-2-methylphenyl)methane; 1,6-hexamethylene diisocyanate; and 3-isocyanatomethyl-3,5,5-trimethylcyclohexyl(isophorone) isocyanate.

Also presented is a method for preparing an interpolymer network delivery system by soaking a foam that includes a polyurethane polymer covalently bound to starch in an iodine-containing solution.

Another embodiment includes a wound dressing having a body facing layer having a body contacting surface and an outwardly facing backing wherein at least a portion of the body contacting surface includes an interpolymer network delivery system. In one embodiment, the interpolymer network delivery system is in the form of a foam.

In another embodiment, the wound dressing further includes an absorbent layer disposed between the body contacting surface and the interpolymer network delivery system.

In yet another embodiment, the wound dressing further includes an antibiotic agent. In still another embodiment, a wound dressing that includes the interpolymer network delivery system is configured for insertion into a body cavity. In another embodiment, a wound dressing that includes the interpolymer network delivery system is configured for insertion into a teat canal of a dairy cow.

Also presented is an implantable medical device that includes the interpolymer network delivery system disposed on at least a portion of the surface of the device. In another embodiment, an insertable medical device includes the interpolymer network delivery system disposed on at least a portion of the surface of the device.

Also presented is a method for treating a wound in a subject by contacting the wound with the interpolymer network delivery system so that iodine is released into the wound. In another embodiment, there is presented a method for treating infected tissue in a subject by contacting the tissue with the interpolymer network delivery system so that iodine is released into the tissue. In still another embodiment, there is presented a method for reducing the likelihood of infection in tissue in a subject susceptible to infection by contacting the tissue with the interpolymer network delivery system so that iodine is released into the tissue.

Also presented is a method for treating mastitis in a dairy cow that includes contacting the interpolymer network delivery system with a teat canal in the cow so that iodine is released into the canal.

DETAILED DESCRIPTION OF THE INVENTION

Figure 1:
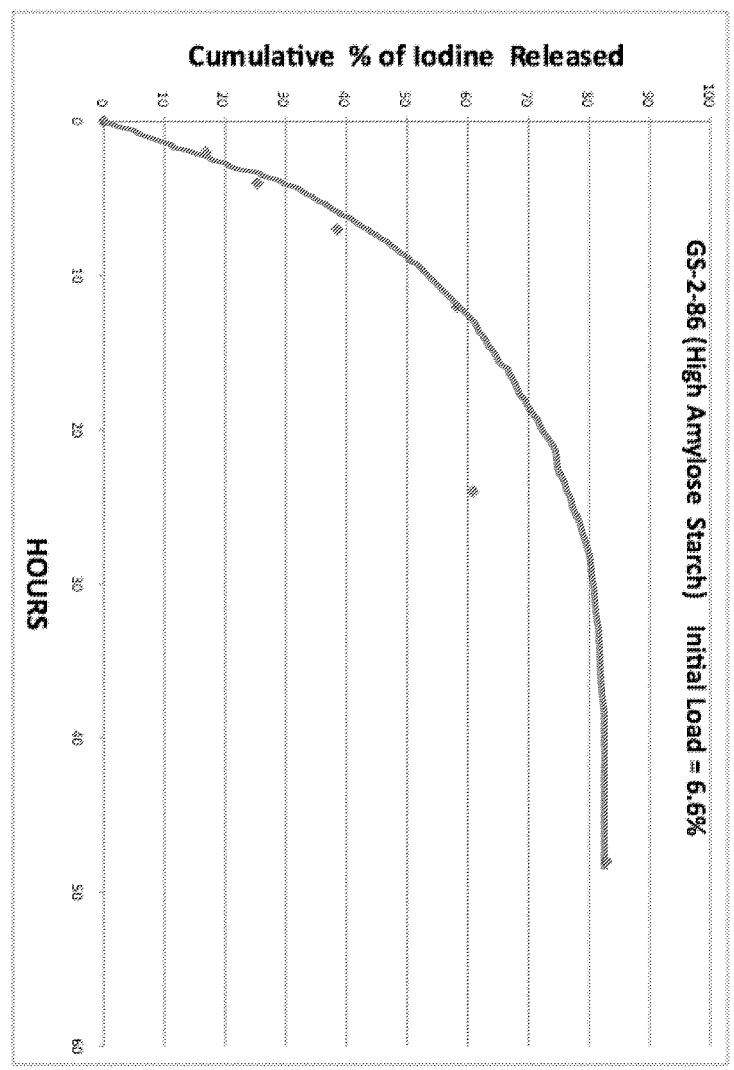
FIG. 1 depicts the cumulative release of iodine from an interpolymer network containing starch with a higher concentration of amylose to amylopectin, 70% amylose to 30% amylopectin, maize starch hybrid.

The present invention relates to an interpolymer network delivery system that includes iodine complexed with starch, wherein the starch is covalently bound to a polyurethane polymer. The concentration of iodine retained in the interpolymer network delivery system can be increased by increasing the concentration of starch in the interpolymer network delivery system. The rate of iodine released from the interpolymer network can be controlled by varying the ratio of amylose to amylopectin that is present in the starch.

As used herein, "starch" is a polysaccharide that includes monosaccharide units joined together by glycosidic bonds. For example, corn starch generally contains from about 20 to about 25% amylose and from about 75 to about 80% amylopectin. The ratio of amylose to amylopectin can vary dependent upon the source (i.e. cereal, root crop, etc.) from which the starch is derived. The cereal may include rice, wheat, corn, maize, or other natural cereal plants. The root crop may include cassava (i.e. tapioca), sweet potato, potato, arrowroot, or other natural root crop plants. In addition to the cereal and the root crop, the starch may also include any plant having starch elements, such as, for example, bananas, barley, sago, sorghum, rye, peas, and mung bean. The ratio of amylose to amylopectin in starch may also be varied by using recombinant methods known in the art.

As used herein, "polyol" includes polymeric polyols and non-polymeric polyols.

As used herein, "polymeric polyols" include industrially produced chemical substances that include a number of molecules linked together with covalent bonds wherein the molecules include at least two hydroxyl groups capable of reacting with a polyisocyanate. Representative examples include (without limitation): polyether, polyester, polyethylene, polyethylene glycol, polypropylene glycol, and polybutylene glycol polyols.

As used herein, "non-polymeric polyol" is defined as a compound having at least two hydroxyl groups capable of reacting with a polyisocyanate. A person of ordinary skill in the art will immediately recognize that numerous chemicals may be used as the polyol in the present invention. Without limiting the scope of the invention, representative examples include ethylene glycol; 1,3-propylene glycol: hexane 1,6-diol; 2 methyl-1,3-propanediol; glycerol; mannitol; sorbitol; diethylene glycol: triethylene glycol; butylene glycol; and dibutylene glycol polyols.

As used herein, "isocyanates" are compounds containing the isocyanate group (—NCO). They react with compounds containing alcohol (hydroxyl) groups to produce polyurethane polymers. Isocyanates useful in the current invention include those that perform as suitable building blocks in polyurethane chemistry such as aromatic, aliphatic, or cycloaliphatic polyisocyanates having at least two active isocyanate groups per molecule. However, a person of ordinary skill in the art will immediately recognize that numerous chemicals may be used as the isocyanate in the present invention. Without limiting the scope of the invention, representative examples include 2,4- and 2,6-diisocyanatotoluene (TDI) and their derivatives; methylenediphenyl 4,4'-, 2,4- and 2,2'-diisocyanates (MDI) and their derivatives; industrial products which may additionally comprise products having more than one ring (polymeric MDI's or PMDI); 1,5-naphthalene diisocyanate (NDI); 4,4',4''-triisocyanatotriphenylmethane and bis(3,5-diisocyanato-2-methylphenyl)methane; 1,6-hexamethylene diisocyanate (HDI); and 3-isocyanatomethyl-3,5,5-trimethylcyclohexyl(isophorone) isocyanate (IPDI). Many such isocyanates are available commercially. For example, commercially available isocyanates include, but are not limited to, isoBind 1088 (Dow Chemical), Isonate 143L (Dow Chemical), PAPI (Dow Chemical), Mondur 541 (Bayer), Lupranate (BASF), and Rubinate (ICI/Huntsman). Furthermore, basic polyisocyanates may also be modified by bi- or trimerization to produce carbodiimides, uretdiones, biurets, and allophanates.

As used herein "cumulative % of release" is the percentage of iodine released from the interpolymer network delivery system as a function of time relative to the amount of iodine present in the interpolymer network delivery system at time 0.

The concentration of the iodine present in the interpolymer network delivery system can be varied according to the concentration of starch. One of ordinary skill in the art will be able to appropriately adjust the ratio of starch to polyols to achieve the desired concentration of starch, and thus vary the concentration of iodine present in the interpolymer network delivery system. A preferred amount of starch in the in the interpolymer network delivery system ranges from about 5% to about 60% by weight of the system. Preferably, the concentration of iodine present in the interpolymer network delivery system ranges from about 1% to about 15% by weight of the system.

The rate of release of iodine from the interpolymer network delivery system can be varied according to the ratio of amylose to amylopectin present in the starch. The greater the ratio of amylose to amylopectin will result in a slower release rate of the iodine that is retained in the interpolymer network delivery system. One with ordinary skill in the art will be able to appropriately adjust the ratio of amylose to amylopectin to achieve the desired release rate of iodine from an interpolymer network delivery system, either choosing a specific type of starch or modifying starch using known recombinant techniques. A preferred range of the ratio of amylose:amylopectin in the starch for an extended release rate of iodine from the interpolymer network deliver), system is from about 50:50 to about 90:10. Alternatively, the range of the ratio of amylopectin:amylose in the starch for a faster initial release rate of iodine from the interpolymer network delivery system is from about 75:25 to about 90:10.

In a further embodiment of the present invention, the interpolymer network delivery system can be produced as a foam or a thin film. As a foam, the interpolymer network delivery system can be used as an absorbent wound dressing.

In a further embodiment of the present invention, the interpolymer network delivery system can retain 50% of iodine that was initially contained within the interpolymer network delivery system for at least 10 hours.

Also presented are methods for preparing the interpolymer network delivery system of the present invention. The steps include: (a) preparing a mixture that includes at least one polyol and at least one isocyanate compound, wherein the isocyanate compound includes at least two active isocyanate groups per molecule; (b) heating the mixture of step (a) to form a prepolymer solution; (c) mixing the prepolymer solution of step (b) with a starch composition that includes starch and water; (d) curing the mixture of step (c) to form an interpolymer; and (e) contacting the interpolymer of step (d) with an iodine-containing solution.

Optionally, the mixture of step (a) further includes a polyurethane catalyst, a solvent, or both. Typical polyurethane catalysts include, but are not limited to, stannous octanoate; dibutyl tin dilaurate; triethyl amine; 1,4-diaza-(2.2.2) bicyclooctane. Typical solvents that can be used include, but are not limited to, ethyl acetate: isopropyl acetate; tetrahydrofuran; and toluene. Additionally or alternatively, the starch composition of step (c) optionally includes a polyurethane catalyst, a surfactant, or both. An optional step includes washing the cured interpolymer of step (d) prior to contacting the interpolymer with the iodine-containing solution.

Preferably, the iodine-containing solution is selected from an aqueous $KI_3$ solution, $I_2$ in methanol, and $I_2$ in ethanol. Alternative iodination methods include the use of a dilute iodine solution (typically ~0.5% by wt.) in 50:50 water: methanol (volume). This method is described in U.S. Pat. No. 3,235,446, the contents of which are incorporated herein by reference in their entirety.

Another method for preparing the interpolymer network delivery system of the present invention includes soaking a foam that includes a polyurethane polymer covalently bound to starch in an iodine-containing solution.

The interpolymer network delivery system of the present invention can be fabricated into different shapes and different sizes and accordingly can be used in many different circumstances. For example, in the form of a flat cloth, it can be a wound dressing or a component of a wound dressing. If fabricated into a cylindrical shape (e.g. plugs and the like), it can be inserted into various body cavities including, but not limited to, the ear canal, nose, rectum or vagina, buccal cavity, the teat canals of the udder of a dairy cow and others.

In one embodiment, the final polymerization/crosslinking step can take place on at least a portion of the surface of an existing medical device such as the surface of a hip implant or the surface of a pace maker. In this way, the described iodine release system can be formulated as an anti-microbial coating. Other suitable medical devices include implantable devices, such as, but not limited to: surgical mesh (e.g. vaginal mesh, hernia mesh, and the like), orthopedic implants (e.g. elbow, knee, shoulder, spine, wrist, and the like), and colostomy stoma appliances. Insertable medical devices are also suitable for use in the present invention. Exemplary devices include, but are not limited to: catheters, cannulas, ports, and needles. In other embodiment, the interpolymer network delivery system can be intentionally shredded and/or ground into small particles which are useful for suspension within a liquid. Such suspensions may be useful in situations where an irregularly shaped cavity needs to be filled with an antimicrobial substance.

The interpolymer network delivery system can be used as a comfortable hydrophilic but insoluble absorbent foam in a wound dressing material for various types of injuries, especially burn related injuries, which in turn results in better patient comfort, because the wound dressing does not have to be frequently changed.

In another embodiment, the present invention also provides for a wound dressing that includes a body facing layer having a body contacting surface and an outwardly facing backing wherein at least a portion of the body contacting surface includes the interpolymer network delivery system. Optionally, the interpolymer network delivery system is in the form of a foam.

Various types of bandages and wound dressings are known and used to protect wounds and burns. Typically, wound dressings are fabricated with an absorbent material so that wound exudate is removed and the wound dried, facilitating healing. Wound dressings may also contain one or more pharmacologically active agents such as antibiotics, local anesthetics, or the like. Commonly used wound dressings include fibrous materials such as gauze and cotton pads, which are advantageous in that they are absorbent but problematic in that fibers may adhere to the wound or newly forming tissue, causing wound injury upon removal. One of the advantages of the present invention is that the wound dressing is easier to remove with less adhesion to the injured tissue or wound. Also, the interpolymer network delivery system used as a foam, the foam can absorb wound exudate further contributing to the healing of a wound.

The interpolymer network delivery system may be a stand alone wound dressing as a foam or preferably form the wound contacting layer of the wound dressing, but it could be any layer that is capable of fluid exchange with the wound surface.

Preferably, the wound dressing of the invention further comprises an absorbent layer and/or a backing layer. The absorbent layer may, for example, be positioned intermediate the interpolymer network delivery system wound contacting layer from the backing layer. Optionally, the wound dressing can also include a antibiotic agent. Antibiotic therapy can be systemic or localized. An antibiotic agent can be delivered separately from the dressing or with it.

The optional absorbent layer may comprise any of the materials conventionally used for absorbing wound fluids, serum or blood in the wound healing art, including gauzes, nonwoven fabrics, superabsorbents, and mixtures thereof. For example, the absorbent layer may be a nonwoven fibrous web, for example a carded web of viscose staple fibers.

Preferably, the wound dressing further comprises a backing layer covering the interpolymer network delivery system and the optional absorbent layer on the side opposite the wound-facing side of the dressing. The backing layer preferably provides a barrier to passage of microorganisms through the dressing and further preferably blocks the escape of wound fluid from the dressing. The backing layer may extend beyond at least one edge of the interpolymer network delivery system and optional absorbent layer to provide an adhesive-coated margin adjacent to the said edge for adhering the dressing to a surface, such as to the skin of a patient adjacent to the wound being treated. An adhesive-coated margin may extend around all sides of the interpolymer network delivery system and optional absorbent layer, so that the dressing is a so-called island dressing. However, it is not necessary for there to be any adhesive-coated margin.

Preferably, the backing layer is substantially liquid-impermeable. The backing sheet is preferably semipermeable. That is to say, the backing sheet is preferably permeable to water vapor, but not permeable to liquid water or wound exudate. Preferably, the backing sheet is also microorganism-impermeable.

Preferably, the adhesive layer extends outwardly from the absorbent layer and the interpolymer network delivery system to form an adhesive-coated margin on the backing sheet around the absorbent layer as in a conventional island dressing. Preferably, the wound dressing according to the present invention is sterile and packaged in a microorganism-impermeable container.

In a further embodiment, the present invention provides for a method of treating a wound in a subject by contacting the wound with the interpolymer network delivery system so that iodine is released into the wound. Exemplary wounds include, but are not limited to: open wounds, burns, cuts, scrapes, pressure ulcers, blisters, incisions, lacerations, abrasions, and the like.

Also presented is a method for treating infected tissue in a subject by contacting the tissue with the interpolymer network delivery system so that iodine is release into the tissue. The devices and methods of the present invention are suitable for any infection that can be treated or ameliorated when contacted with iodine. Exemplary infectious conditions include, but are not limited to: lesions, non-healing ulcers, methicillin-resistant *Staphylococcus aureus* (MRSA), mastitis, microbial viruses, bacterial infections, fungal infections, yeast infections, and the like. A method for reducing the likelihood of infection in tissue in a subject susceptible to infection by contacting the tissue with the interpolymer network delivery system of the present invention so that iodine is released into the tissue is also presented.

As used herein, the term "subject" includes human and non-human patients. Mammalian and non-mammalian (including, e.g., Aves) patients are also suitable. The present invention may find wide application in veterinary medicines to treat a variety of wounds and infections in a mammalian animal, including but not limited to, horses, dogs, cats, or any other domestic or wild mammalian animals.

For example, dairy cows do not produce milk constantly. When these animals go into their "dry period", they are susceptible to "mastitis", an infection of the teats of their udder. To reduce the frequency of these infections, a tampon-like device that incorporates the interpolymer network delivery system of the present invention can be inserted into the inner lumen (canal) of the teat, releasing iodine and thereby preventing the colonization of this space by invading bacteria.

In dogs, the ear canal is sometimes infected (otitis) and some animals are particularly prone to such infections. The insertion of a soft, rubbery embodiment of the interpolymer network delivery system described herein can be used to both treat an existing infection and prevent ear canal infections (otitis) from occurring.

The following non-limiting examples serve to further illustrate the present invention.

EXAMPLES

Example 1

Preparation of Interpolymer Network Delivery System—Prepolymer Method

Part a: Isocyanate Terminated Prepolymer

A 250 ml three neck round bottom flask was equipped with a mechanical stirrer, a thermometer, water cooled reflux condenser with drying tube and a nitrogen inlet tube/bubbler assembly. To this reactor assembly was added:
  20 gm. Polycaprolactone triol of molecular weight 900 Daltons
  20 gm. Polycaprolactone diol of molecular weight 530 Daltons
  20 gm. Poly(ethylene oxide) 200 adipate diol of molecular weight 530 Daltons
  36.8 gm 2,4-toluene diisocyanate
  24.2 gm. Ethyl acetate The reaction mixture was mixed and heated at 60-65° C. until analysis by infrared spectroscopy indicated the complete disappearance of hydroxyl functionality. Heating was discontinued after 3 hours as the reaction was complete. The prepolymer solution (80% solids) was cooled to room temperature under nitrogen sweep and analyzed for % NCO content. % NCO=6.72% on the 80% solids basis. Starting material variations for producing alternative prepolymer compositions according to the method of Part A are provided below in Table 1.

TABLE 1

Starting material variations for Example 1-Part A. (all ingredients in grams)

| Ingredient | Example 1-2 | Example 1-3 | Example 1-4 | Example 1-5 | Example 1-6 | Example 1-7 | Example 1-8 |
|---|---|---|---|---|---|---|---|
| P-1 | 30 | — | 10 | 20 | 20 | 10 | 10 |
| P-2 | — | 25 | 10 | 20 | 20 | 10 | 10 |
| P-3 | — | 5 | — | — | — | — | — |
| P-4 | — | — | — | — | — | — | — |
| P-5 | — | — | 10 | 20 | 20 | 10 | 10 |
| TDI | 16.1 | 16.1 | 30.6 | 36.8 | 36.8 | 18.5 | 17.6 |
| Ethyl acetate | 19.8 | 19.7 | 15.2 | 24.2 | 24.2 | 12.1 | 11.9 |
| % solids | 70.0% | 70% | 80% | 80% | 80% | 80% | 80% |
| % NCO @100% | NA | 8.2% | 8.5% | 8.5% | 6.7% | 6.7% | 8.3% |
| Expt. # | GS-2-90 | GS-2-92 | GS-3-13 | GS-3-32 | GS-3-33 | GS-3-55 | GS-3-81 |

Polyol Types
P-1 polycaprolactone triol Mw = 900
P-2 polycaprolactone diol Mw = 530
P-3 poiycaprolactone diol Mw = 2000
P-4 = Glycerin
P-5 = polyethyleneglycol 600 adipate diol Mw = 530

Part B: Foam Interpolymer Preparation

An open 250 ml glass beaker equipped with a stainless steel propeller type agitator and high speed stirrer motor was charged with 15 gm distilled water. 20 gm of a pre-cooked high amylose starch powder @10% moisture was slowly sifted into the water with good agitation (1000 rpm) to form a starch paste. The starch used was a 10% propyleneoxide treated 70% amylose fluidity corn starch with Mn=4000

Daltons and a polydispersity of 1.9. The addition of dry starch to the water took 10 minutes. To the resulting starch paste 0.7 gm of Tween 80 surfactant and 0.35 gm of DABCO polyurethane catalyst was added with mixing. To this mixture at 25° C., 46 gm of the prepolymer solution from Part A was added over a period of one minute with the stirring speed set at 100 rpm. Mixing was continued for an additional 3 minutes. The emulsified reaction mixture was poured out on to a release paper surface and drawn down as a film using an adjustable film applicator set at 0.2 inch clearance. The wet film was allowed to cure and foam at room temperature in a forced draft hood for 36 hours. After the curing time, the foam was washed thoroughly in distilled water until the rinse water showed a negative iodine test for the presence of starch. The washed foam was left to dry in a forced draft hood at room temperature overnight. The foam had the following characteristics:

Weight % starch=35%
Foam density=0.17 gm/cubic centimeter closed cell
Water uptake=130% weight increase
% strain at break=70%
Stress yield at break=0.11 megapascals
Modulus (5%)=7850 kilopascals Starting material variations for producing alternative interpolymer compositions according to the method of Part B are provided below in Table 2.

the temperature at 25° C. The resulting paste was poured on to a smooth release paper surface and drawn down as a film using a six inch wide adjustable gap set at 0.2 inch clearance. The product was dried and cured in a well-ventilated hood for 2 days. After washing with distilled water to remove any unreacted starch, the foam product was treated with $KI_3$ solution as in Example 2. The release characteristics of the iodinated foam are shown in FIG. 2.

Using the same procedure and ratio of ingredients, a high amylose containing composition was prepared by substituting the acid hydrolyzed waxy starch in the example above with an acid hydrolyzed 70% amylose 10% propylene oxide modified corn starch. The release characteristics of the final iodinated foam product are shown in FIG. 1. These two compositions now differ only in the starch type used in the formulation.

Figure 2:
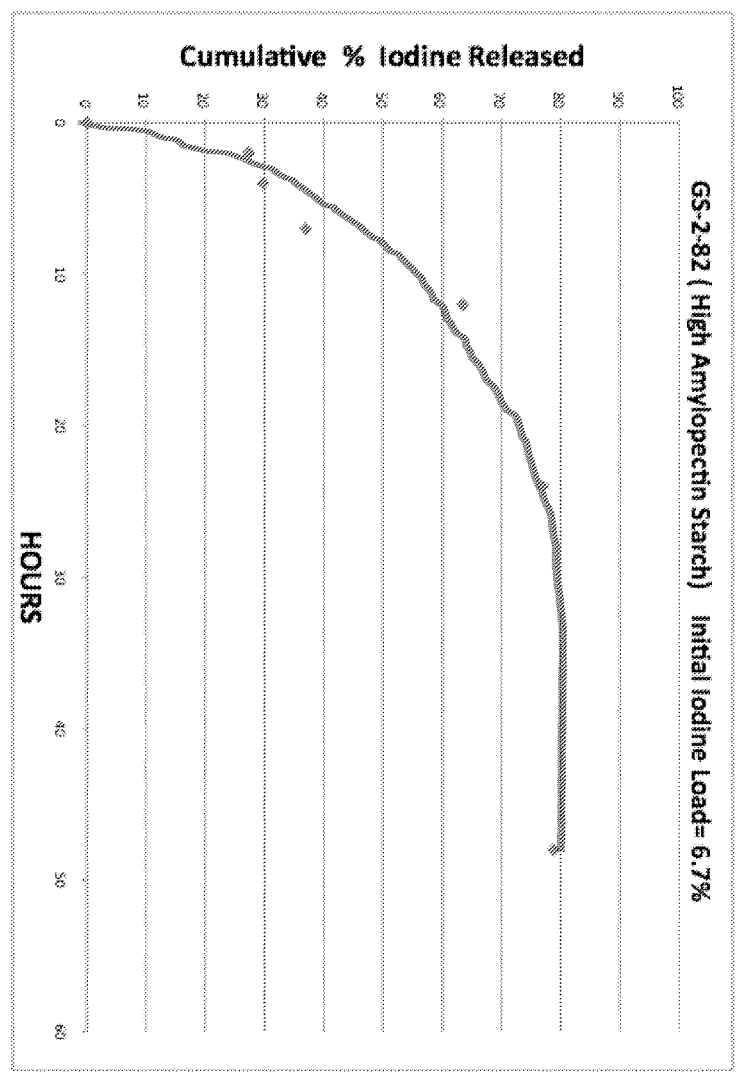
FIG. 2 depicts the cumulative release of iodine from an interpolymer network containing starch with a lower concentration of amylose to amylopectin, waxy maize starch 10% amylose and 90% amylopectin.
Figure 3:
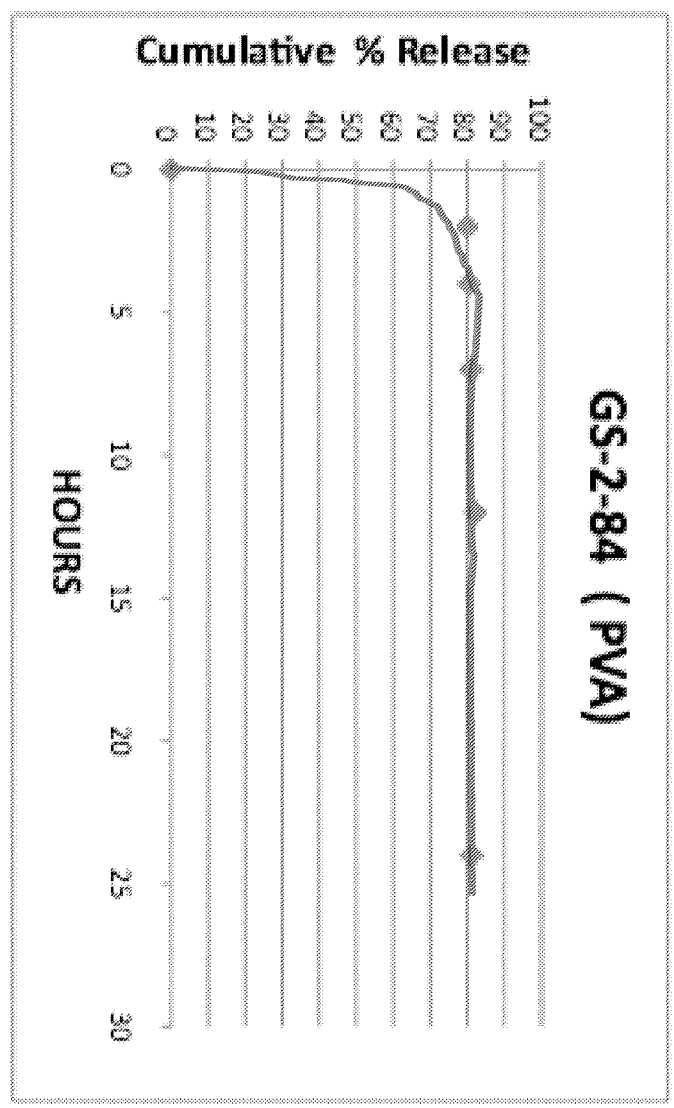
FIG. 3 depicts the release of iodine from an acetalized polyvinyl alcohol iodine complex of the type described in U.S. Pat. No. 5,071,648.
Figure 4:
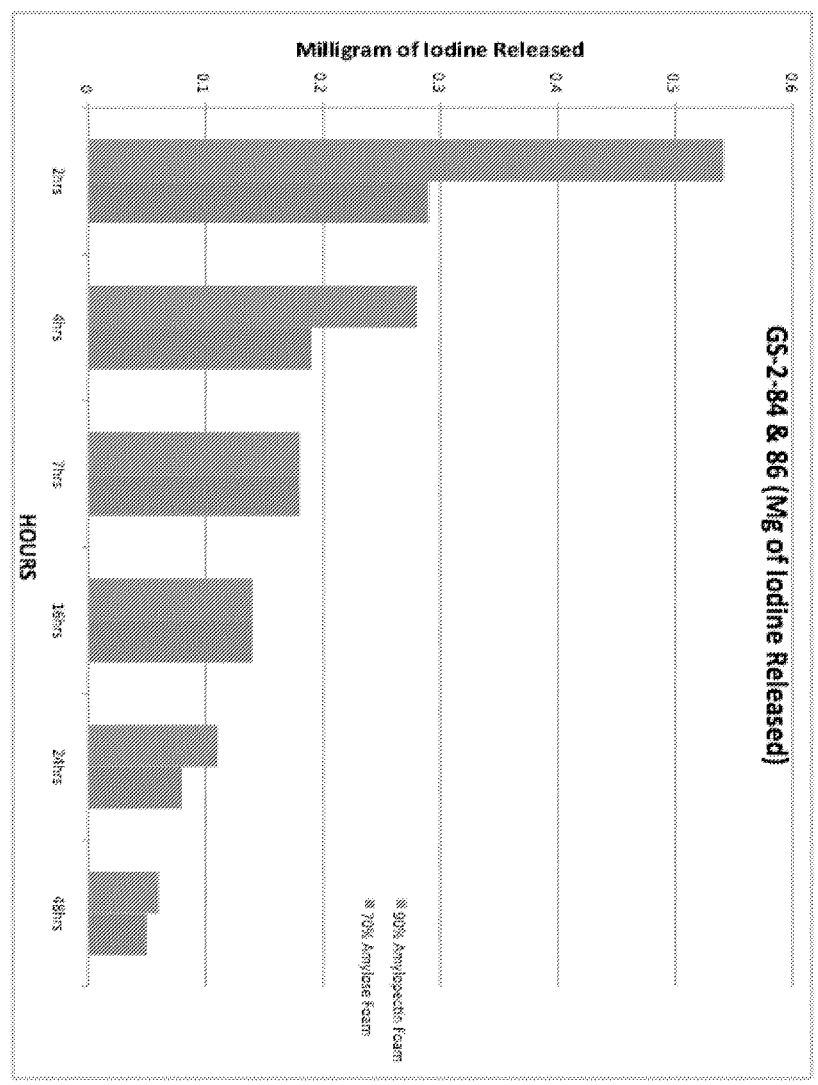
FIG. 4 provides an iodine release rate comparison between the 70% amylose to 30% amylopectin composition and the 10% amylose and 90% amylopectin.
Figure 5:
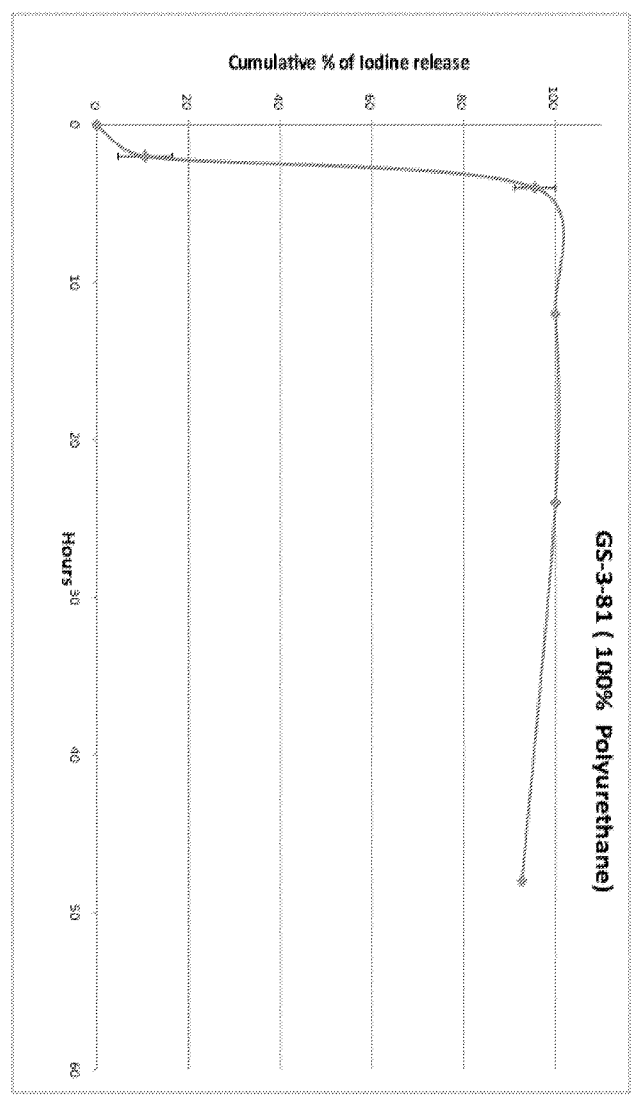
FIG. 5 depicts the release of iodine from a 100% polyurethane composition prepared according to Example 1-8.
Figure 6:
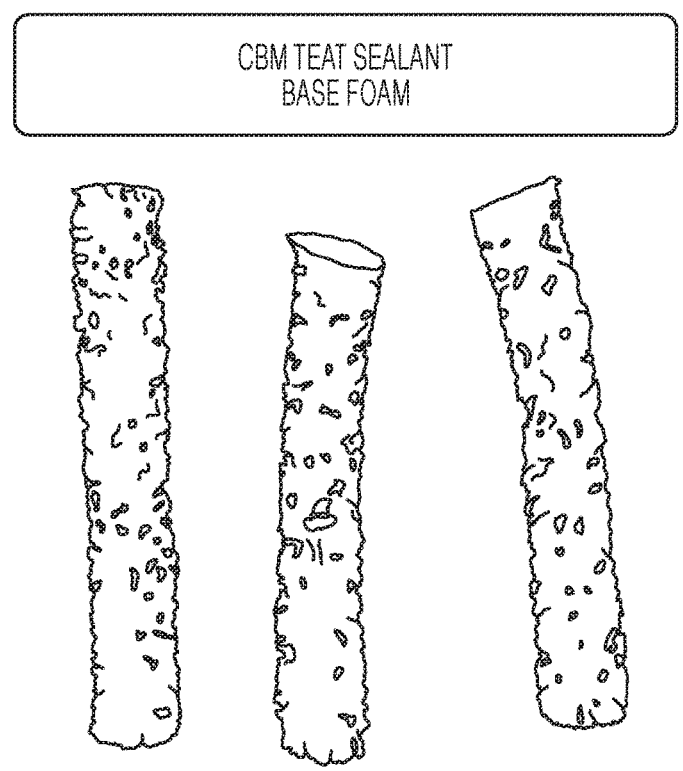
FIG. 6 is a photograph of an 8 mm diameter pre-iodinated base foam device configured for use as a small cavity anti-microbial insert for non-lactating dairy cows.
Figure 7:
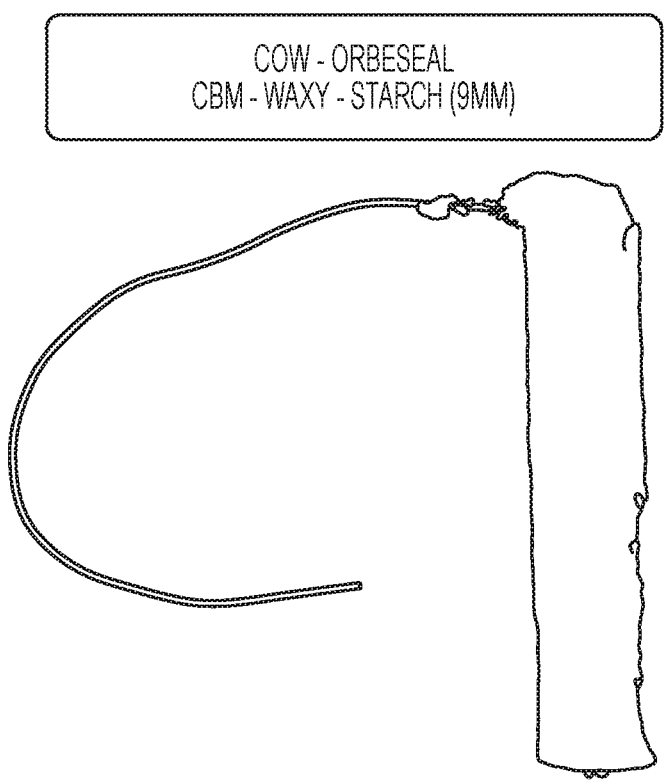
FIG. 7 is a photograph of a 9 mm diameter pre-iodinated base foam device configured for use as a small cavity anti-microbial insert for non-lactating dairy cows and further configured with a string device for ease of removability from the animal.
Figure 8:
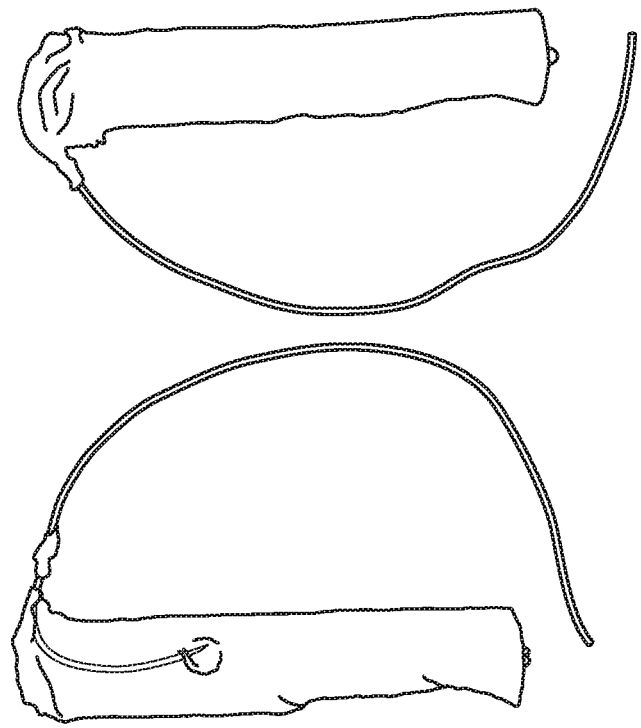
FIG. 8 is a photograph of device as in FIG. 7 with fuller view of the string extraction device.
Figure 9:
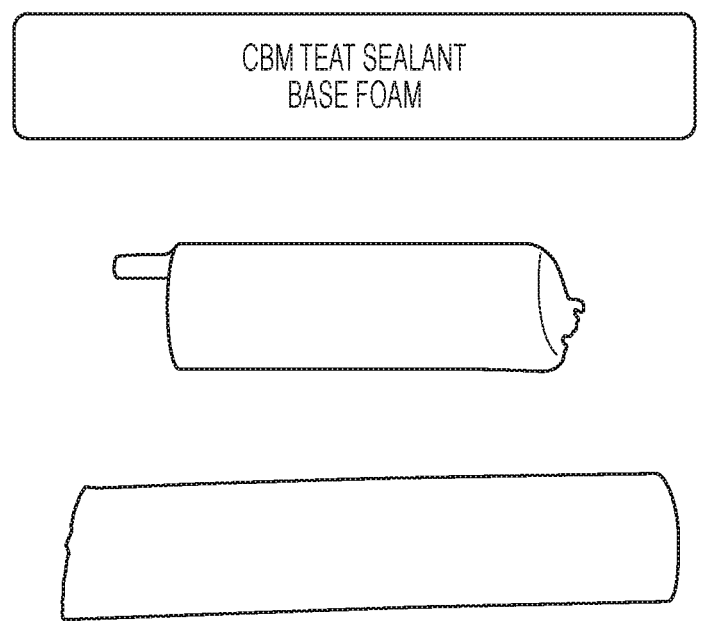
FIG. 9 is a photograph of a 13 mm pre-iodinated base foam device for use in larger diameter cavities. The top device is constructed with a fully exposed foam surface while the device on the bottom is constructed with a surface skin for greater smoothness and ease of insertion and removal.
Figure 10:
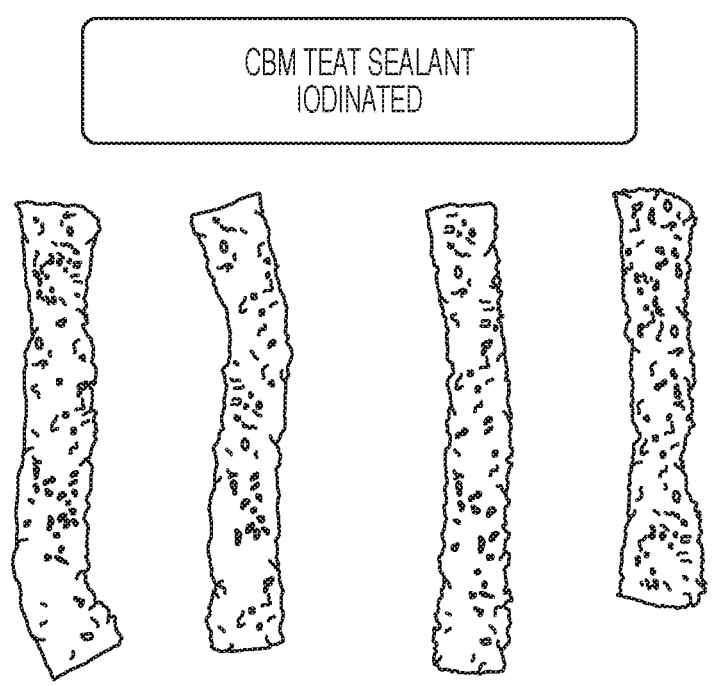
FIG. 10 is a photograph of an 8 mm diameter iodinated foam device configured for use as a small cavity anti-microbial insert for non-lactating dairy cows.

As shown by comparing FIGS. 1 and 2, the cumulative release rate of the high amylopectin based foam (FIG. 2) is faster than the release rate of the high amylose based foam (FIG. 1) especially in the early stages of the time profile. This effect is more clearly demonstrated in FIG. 4 which exhibits the milligrams of iodine released at each time point. The amylopectin based foam clearly releases iodine at a faster rate in the beginning of the study while the high amylose based foam exhibits a more even and sustained dose rate.

TABLE 2

Starting material variations for Example 1-Part B. (all ingredients in grams)

| Ingredient | Example 1-2 | Example 1-3 | Example 1-4 | Example 1-5 | Example 1-6 | Example 1-7 | Example 1-8 |
|---|---|---|---|---|---|---|---|
| S-1 | — | 15 | 25 | — | — | — | — |
| S-2 | 15 | — | — | 20 | — | 4.0 | — |
| S-3 | — | — | — | — | 20 | — | — |
| DI Water | 7.5 | 7.5 | 15 | 15 | 15 | 4.0 | 6 |
| Glycerin | 7.5 | 7.5 | — | — | — | — | 6 |
| Tween 80 | 0.6 | 0.85 | 0.5 | 0.7 | 0.7 | 0.7 | 0.3 |
| DABCO | 0.6 | 0.2 | 0.2 | 0.35 | 0.35 | 0.35 | 0.17 |
| Prepolymer solution | 32.0 | 32.1 | 31.3 | 46.0 | 46.0 | 45.0 | 23.0 |
| Expt. # | GS-2-90 | GS-2-92 | GS-3-13 | GS-3-32 | GS-3-33 | GS-3-55 | GS-3-81 |

Starch Types
S-1 = acid hydrolyzed waxy maize (number avg. MW (Mn) = 28 kDa and PD = 2.5)
S-2 = acid hydrolyzed high amylose (70%) maize 10% propylene oxide treated (Mn = 4 kDa and PD = 1.9)
S-3 = potato maltodextrin (Mn = 3 kDa)

Although the prepolymer method shown here is the preferred method, interpolymer foams can also be prepared by a batch method (Part C below) where all the synthetic polyols are preemulsified with the starch, water, surfactant and catalyst ingredients. This preemulsion is mixed thoroughly with the isocyanate ingredient and then poured into a mold or cast into a film and allowed to cure.

Part C: Preparation of Interpolymer Network Delivery System—Batch Method

An open 500 ml glass beaker equipped with a stainless steel propeller type agitator and high speed stirrer motor was charged with 20 gm distilled water and 20 gm glycerin. With stirring, 40 gm of an acid hydrolyzed 90% amylopectin corn starch (Mn=21 kDa, Polydispersity=1.9) was mixed into the water glycerine mixture being careful not to form lumps. To this mixture, was added 1.8 gm Tween 80 surfactant, 0.8 gm DABCO catalyst and 40 gm of polycaprolactone triol Mw=900 (polyol P-1). This mixture was stirred for about 10 minutes at 1000 rpm to form a smooth paste mixture. To this paste was added 20 gm 2,4-toluene diisocyanate and the mixture agitated for three minutes at 1000 rpm maintaining Example 2

Preparation of Interpolymer Network Delivery System Containing Iodine 40 gm. of washed and dried interpolymer foam is placed in a glass tray and soaked for 4 hours in 500 ml of an 2% aqueous $KI_3$ solution*. After the soaking period, the blue/black colored foam is removed from the treatment bath and washed continuously with room temperature distilled water until the rinse water from the washings shows only a very slight iodine response to starch indicator solution. The treated foam is dried in a forced draft hood overnight at room temperature. The bound iodine content was determined to be 9.89% by weight.

*2% $KI_3$ Solution: Take 20 gm. iodine and 40 gm potassium iodide in a 2 liter amber bottle and add 2000 ml of distilled water. Stir overnight at room temperature. Store in the dark.

Table 3 provides a listing of characteristics of various interpolymer network delivery systems prepared according to the methods of Examples 1(A) and (B) and 2.

TABLE 3

Characterization of Interpolymer Network Delivery System.

| Co-polymer composition wt. % | Example 1-2 | Example 1-3 | Example 1-4 | Example 1-5 | Example 1-6 | Example 1-7 | Example 1-8 (comparative) |
|---|---|---|---|---|---|---|---|
| Starch S-1 | — | 33.3% | 50% | — | — | — | — |
| Starch S-2 | 33.3% | — | — | 35% | — | 10% | — |
| Starch S-3 | — | — | — | — | 35% | — | — |
| Polyol P-1 | 32.5 | — | 10.3 | 13.7 | 13.7 | 18.5 | 15.8 |
| Polyol P-2 | — | 27.1 | 10.3 | 13.7 | 13.7 | 18.5 | 15.8 |
| Polyol P-3 | — | 5.4 | — | — | — | — | — |
| Polyol P-4 | 16.7 | 16.7 | — | — | — | — | 34.6 |
| Polyol P-5 | — | — | 10.3 | 13.7 | 13.7 | 18.5 | 15.8 |
| TDI | 17.5 | 17.5 | 19.1 | 24.7 | 24.7 | 34.5 | 28.0 |
| % Water Extractables | 35% | 29% | 10% | 22% | 19% | 9% | 0% |
| Foam density gm/cm$^3$ | 0.43 | 1.11 | 0.44 | 0.17 | 0.35 | 0.11 | 0.15 |
| % water absorbed | 200% | 35% | 83% | 127% | 38% | 150% | NA |
| % strain @ break | 152% | 24% | 34% | 70% | 58% | NA | 64% |
| Yield stress Kpa | 200 | 400 | 150 | 110 | 180 | NA | 230 |
| Young's modulus Kpa | 6900 | 4000 | 7090 | 7850 | 8350 | NA | 7333 |
| Experimental # | GS-2-90 | GS-2-92 | GS-3-13 | GS-3-32 | GS-3-33 | GS-3-55 | GS-3-81 |
| % Iodine | 6.4% | 6.2% | 11.7% | 9.9% | 5.0% | — | 1.6% |
| Time to 80% cum. Release (Hours) | 35 | 35 | 50 | 40 | 25 | — | 3 |

Example 3

Determination of Cumulative Iodine Release in 10% BSA Solution

Chemicals Required:
0.1 N sodium thiosulfate (purchased Sigma Aldrich)
0.1 N iodine solution (purchased Sigma Aldrich)
starch indicator solution (purchased Sigma Aldrich)
10% BSA solution: Add 100 gm of BSA (Sigma Aldrich) to a 2000 ml beaker. To this, add 100 ml of PBS 7.4 pH buffer solution. Mix at 250 rpm for 30 minutes. Transfer to a storage container for use as the medium for the release studies.
PBS tablets (purchased from MP Pharmaceuticals)
Procedure:
Cut the interpolymer foam into square pieces each weighing between 0.5-1.0 gm. Since the released at each timepoint is determined by determining the iodine remaining in triplicate samples at each time point, a sufficient number of foam sample squares should be prepared. Place each analytically weighed sample into a 250 ml bottle, add 150 ml 10% BSA solution and cap the bottle. Place the bottles in a temperature controlled water bath shaker (70 rpm). At predetermined time intervals, remove bottles from the shaker, remove foam sample, squeeze well. Each sample is cut into small pieces and placed into a clean 250 ml bottle containing 25.00 ml 0.1N sodium thiosulfate solution. Place these back in a 37° C. water bath shaker for 48 hours to extract all remaining iodine from the sample. After 48 hrs at 37° C., proceed with the back titration below.
At the same time, change the release medium of the continuing time point samples in order to maintain sink conditions (add 150 ml of fresh 10% BSA solution) and continue to shake at 25° C. until next time point.
Back titration: after the 48 hours at 37° C., remove the sample from the shaker, cool to room temperature and add 100 ml distilled water. Gravity filter the foam away from the thiosulfate solution into an Erlenmeyer flask using VWR #415 coarse paper. Add 3 drops of starch indicator solution and titrate to the starch iodine end point using the 0.1 N iodine solution. Run blank without sample.

% iodine remaining=(ml blank−sample)×N thiosulfate×12700/sample wt gms

% cumulative iodine released=% iodine at zero time−% iodine remaining at time $t_x$.

Timepoints: 2, 4, 7, 16, 24 and 48 hours

Example 4

Treatment of Wounds with a Wound Dressing

Partial thickness dermatomal wounds (1.25 mm deep) were created in a porcine model. Wounds were inoculated with 0.1 mL of *Staph aureus* (ACCT 29213; 1 million CFU/mL). Dressings were changed every 48 hours. On days 2, 4 and 7 after injury, superficial wound cultures and full thickness 4 mm punch biopsies of the wounds were taken. Semi-quantitative bacterial counts were obtained from all wounds. Histopathological studies were also done on H&E stained sections.

Wounds treated with a prototype iodine-releasing wound dressing were equivalent in terms of re-epitheliazation on day 2 compared to wounds treated with Silverlon®. The iodine dressings had the highest level of infection control on day 2 compared to any other dressing within the treatment groups. Wounds treated with either Silverlon® or iodine dressings exhibited much faster re-repitheliazation rates compared to infected controls, confirming that infection control is critical. About 50% of the complexed iodine remained within the dressing after 2 days, confirming the sustained release of iodine. No inflammation/irritation was observed in the iodine-treated wounds.

Iodine and Silverlon® dressings were superior in the pig model to controls without antimicrobial activity. In terms of infection control, the iodine dressing seemed to be superior to the Silverlon® dressing. Both Silverlon® and iodine dressings promoted re-epitheliazation.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A wound dressing configured for insertion into a body cavity comprising an interpolymer network delivery system, said interpolymer network delivery system consisting essentially of iodine, starch and a polyurethane polymer, wherein said iodine is complexed with said starch, said starch is covalently bound to said polyurethane polymer, and the ratio of amylose to amylopectin in the starch ranges from about 50:50 to about 90:10.

2. The wound dressing of claim 1, wherein said iodine is present in an amount from about 1% to about 15% by weight of the system.

3. The wound dressing of claim 1, wherein the starch is present in an amount from about 5% to about 60% by weight of the system.

4. The wound dressing of claim 1, wherein the starch is derived from a cereal selected from the group consisting of rice, wheat, and maize.

5. The wound dressing of claim 1, wherein the polyurethane polymer is derived from a polymeric polyol selected from the group consisting of polyether, polyester, polyethylene, polyethylene glycol, polypropylene glycol, and polybutylene glycol polyols.

6. A method for preparing the interpolymer network delivery system of claim 1 comprising:
   (a) preparing a mixture comprising at least one polyol and at least one isocyanate compound, wherein the isocyanate compound comprises at least two active isocyanate groups per molecule;
   (b) heating the mixture of step (a) to form a prepolymer solution;
   (c) mixing the prepolymer solution of step (b) with a starch composition comprising starch and water;
   (d) curing the mixture of step (c) to form an interpolymer; and
   (e) contacting the interpolymer of step (d) with an iodine-containing solution.

7. The method of claim 6, wherein the mixture of step (a) further comprises a polyurethane catalyst, a solvent, or both.

8. The method of claim 6, wherein the starch composition of step (c) further comprises a polyurethane catalyst, a surfactant, or both.

9. The method of claim 6 further comprising washing the cured interpolymer of step (d) prior to contacting the interpolymer with the iodine-containing solution.

10. The method of claim 6, wherein the iodine-containing solution is selected from the group consisting of an aqueous $KI_3$ solution, $I_2$ in methanol, and $I_2$ in ethanol.

11. The method of claim 6, wherein the isocyanate compound is selected from the group consisting of 2,4-diisocyanatotoluene; 2,6-diisocyanatotoluene; methylenediphenyl 4,4'-diisocyanate; methylenediphenyl 2,4-diisocyanate; methylenediphenyl 2,2'-diisocyanate; 1,5-naphthalene diisocyanate; 4,4',4''-triisocyanatotriphenylmethane; bis(3,5-diisocyanato-2-methylphenyl)methane; 1,6-hexamethylene diisocyanate; and 3-isocyanatomethyl-3,5,5-trimethylcyclohexyl(isophorone) isocyanate.

12. The method of claim 6, wherein the starch is derived from a cereal selected from the group consisting of rice, wheat, and maize.

13. The method of claim 6, wherein the ratio of amylose to amylopectin in the starch ranges from about 50:50 to about 90:10.

14. A method for preparing the interpolymer network delivery system of claim 1 comprising soaking a foam comprising a polyurethane polymer covalently bound to starch in an iodine-containing solution.

15. The method of claim 14, wherein the ratio of amylose to amylopectin in the starch ranges from about 50:50 to about 90:10.

16. A wound dressing comprising a body facing layer having a body contacting surface and an outwardly facing backing wherein at least a portion of the body contacting surface comprises an interpolymer network delivery system, said interpolymer network delivery system consisting essentially of iodine, starch and a polyurethane polymer, wherein said iodine is complexed with said starch, said starch is covalently bound to said polyurethane polymer, and the ratio of amylose to amylopectin in the starch ranges from about 50:50 to about 90:10.

17. The wound dressing of claim 16, wherein the interpolymer network delivery system is in the form of a foam.

18. The wound dressing of claim 16 further comprising an absorbent layer disposed between the body contacting surface and the interpolymer network delivery system.

19. An implantable medical device comprising a interpolymer network delivery system disposed on at least a portion of the surface of the device, said interpolymer network delivery system consisting essentially of iodine, starch and a polyurethane polymer, wherein said iodine is complexed with said starch, said starch is covalently bound to said polyurethane polymer, and the ratio of amylose to amylopectin in the starch ranges from about 50:50 to about 90:10.

20. A method for treating a wound in a subject comprising contacting the wound with the interpolymer network delivery system of claim 1 so that iodine is released into the wound.

21. A method for treating infected tissue in a subject comprising contacting the tissue with the interpolymer network delivery system of claim 1 so that iodine is released into the tissue.

22. A method for reducing the likelihood of infection in tissue in a subject susceptible to infection comprising contacting the tissue with the interpolymer network delivery system of claim 1 so that iodine is released into the tissue.

23. A method for treating mastitis in a dairy cow comprising contacting the interpolymer network delivery system of claim 1 with a teat canal in the cow so that iodine is released into the canal.

24. The wound dressing of claim 16, wherein said iodine is present in an amount from about 1% to about 15% by weight of the interpolymer network delivery system.

25. The wound dressing of claim 16, wherein the starch is present in an amount from about 5% to about 60% by weight of the interpolymer network delivery system.

26. The wound dressing of claim 16, wherein the starch is derived from a cereal selected from the group consisting of rice, wheat, and maize.

27. The wound dressing of claim 16, wherein the polyurethane polymer is derived from a polymeric polyol selected from the group consisting of polyether, polyester, polyethylene, polyethylene glycol, polypropylene glycol, and polybutylene glycol polyols.

* * * * *